(12) United States Patent
Hussainova et al.

(10) Patent No.: US 10,370,640 B2
(45) Date of Patent: Aug. 6, 2019

(54) SELF-ALIGNED FIBROUS SCAFFOLDS FOR AUTOMECHANOINDUCTION OF CELL CULTURES

(71) Applicant: Tallinn University of Technology, Tallinn (EE)

(72) Inventors: Irina Hussainova, Tallinn (EE); Michael Gasik, Tallinn (EE); Roman Ivanov, Tallinn (EE)

(73) Assignee: Tallinn University of Technology, Tallinn (EE)

( * ) Notice: Subject to any disclaimer, the term of this patent is extended or adjusted under 35 U.S.C. 154(b) by 189 days.

(21) Appl. No.: 15/644,954

(22) Filed: Jul. 10, 2017

(65) Prior Publication Data

US 2018/0016551 A1 Jan. 18, 2018

Related U.S. Application Data

(60) Provisional application No. 62/361,015, filed on Jul. 12, 2016.

(51) Int. Cl.
*C12N 5/0793* (2010.01)
*C12N 5/09* (2010.01)
*G01N 33/50* (2006.01)
*C12N 5/00* (2006.01)
*C12N 5/0786* (2010.01)
*C12N 5/0775* (2010.01)

(52) U.S. Cl.
CPC ......... *C12N 5/0619* (2013.01); *C12N 5/0068* (2013.01); *C12N 5/0645* (2013.01); *C12N 5/0667* (2013.01); *C12N 5/0693* (2013.01); *G01N 33/5005* (2013.01); C12N 2503/00 (2013.01); C12N 2506/1346 (2013.01); C12N 2513/00 (2013.01); C12N 2527/00 (2013.01); C12N 2533/00 (2013.01); C12N 2533/10 (2013.01); C12N 2533/30 (2013.01); C12N 2535/10 (2013.01)

(58) Field of Classification Search
CPC .......... C12N 2503/00; C12N 250/1346; C12N 2513/00; C12N 2527/00; C12N 2533/00; C12N 2533/10; C12N 2533/30; C12N 2535/10; C12N 5/0068; C12N 5/0619; C12N 5/0645; C12N 5/0667; C12N 5/0693; G01N 33/5005; H02J 9/062; H02M 5/4584; H02M 7/5387; A61L 27/04

See application file for complete search history.

(56) References Cited

PUBLICATIONS

Chen et al. Materials Sci.Engineer. C (2010) 30: 647-656 (Year: 2010).*
Aghayan Marina et al., Coupled thermal analysis of novel alumina nanofibers with ultrahigh aspect ratio, Thermochimica Acta 574 (2013), pp. 140-144.
Talukdar Yahfi et al., The Effects of Graphene Nanostructures on Mesenchymal Stem Cells, Biomaterials. Author manuscript, available in PMC Jun. 1, 2015.
Breassan Eriberto et al., Graphene based scaffolds effects on stem cells commitment, Journal of Translational Medicine, 2014, 12:296.
Discher Dennis at al., Tissue Cells Feel and Respond to the Stiffness of Their Substrate, Science vol. 310, Nov. 18, 2005.
Lee Jungwoo et al., Three-Dimensional Cell Culture Matrices—State of the Art, Tissue Engineering; Part B, vol. 14, No. 1, 2008.
Kazantseva Jekaterina et al., Alternative splicing targeting the hTAF4-TAFH domain of TAF4 Represses Profileration and Accelerates Chondrogenic Differentiation of Human Mesenchymal Stem Cells, The Chinese Univeristy of Hong Kong, China; Published Oct. 2, 2013.
Paraic A. Kenny et al., The morphologies of breast cancer cell lines in three-dimensional assays correlate with their profiles of gene expression, Mol Oncol. Jun. 2007.
Smith Callahan Laura et al., Directed differentiation and neurite extension of mouse embryonic stem cell on aligned poly(lactide) nanofibers functionalized with YIGSR peptide; Biomaterials 34 (2013), pp. 9089-9095.
Coulombe Pierre et al., Cytoplasmic intermediate filaments revealed as dynamic and multipurpose scaffolds; Nature Cell Biology vol. 6 No. 8, Aug. 2004; pp. 699-706.
Jin Guorui et al., The electrically conductive scaffold as the skeleton of stem cell niche in regenerative medicine; Materials Science and Engineering C45 (2014) pp. 671-681.

* cited by examiner

*Primary Examiner* — Susan M Hanley
(74) *Attorney, Agent, or Firm* — Berggren LLP

(57) ABSTRACT

Self-aligned fibrous scaffolds are disclosed. The scaffolds are capable of automechanoinduction of cell cultures and methods to induce authomechanoinduction in cancer cells and stem cells are disclosed as well.

14 Claims, 2 Drawing Sheets

SELF-ALIGNED FIBROUS SCAFFOLDS FOR AUTOMECHANOINDUCTION OF CELL CULTURES

PRIORITY

This application claims priority of the U.S. provisional application No. 62/361,015 filed on Jul. 12, 2016, the contents of which is incorporated herein by reference.

FIELD OF THE INVENTION

The present invention relates to biotechnology and applied biology, particularly to cell culturing systems, and more particularly to multi-dimensional cells culture systems using specially prepared fibrous supports (scaffolds).

BACKGROUND OF THE INVENTION

Regenerative medicine and cell therapy represent a breakthrough change in paradigm in healthcare compared to more traditional pharmacology approach [1]. The role of proper in vitro protocols and systems for cells and drugs research is vital in creation of cost-effective and scientifically validated treatment methods, at the same time refining, reducing and replacing ("3R") expensive and scattered animal studies and long expensive clinical trials.

For efficient cell adhesion, proliferation, morphogenesis and differentiation, scaffolds should properly mimic natural in vivo microenvironments and offer local conditions needed for regulation of cellular functions [1,2,3,4]. Besides other factors, the surface and topography of a scaffold affects greatly stem cell specification [3] (for example, a fibrous scaffold was found to increase neural stem cell oligodendrocyte differentiation as well as greatly improve neurite extension and gene expression for neural markers [4]). For example, U.S. Pat. No. 8,148,122 describes flat polymeric, randomly oriented fibers type substrates for cells culturing.

The specific niches with conductive surfaces can promote human mesenchymal stem cells (hMSC) differentiation towards electro-active lineages [3,4,5], opening new scenarios for regeneration of neural, cardiac and similar tissues and capable to assist drug research in vitro. For cells behavior analysis (stem cells proliferation and fate; cancer cells attachment and growth; gene expressions variations, etc.), many properties of 3D scaffolds are essential. For example, substrate stiffness and topology are well known to modulate primary cells shape and morphology with conditions required for further specific differentiation. However, their explicit interactions with cells and extracellular matrix (ECM) system are too complex to allow specific parameters to be separated to a reliable extent.

Many approaches to establish three dimensional (3D) cell culture systems have been undertaken with the major aim to mimic the ECM and configuration and to give structural, dimensional stability to the cells in the culture. Most of them concern gel and collagen systems, polymeric nanofiber scaffolds and porous scaffolds (for example, as shown in U.S. Pat. No. 6,337,198) that intend to promote 3D cell growth [6,7,8]. All of these platforms developed to date, however, have distinct disadvantages such as cell aggregation, low cell survival or experimental limitations. One of the disadvantages is also a high specific response of the cell type to one or another scaffold type, which drives to use many different materials and systems for different cultures making it challenging to compare the results.

The fibrous scaffolds recently gain more attention as they allow more variation in fiber diameter, packing density, porosity, surface state etc. to be tailored for specific needs. For example, US patent application US 20060263417 describes 'Electrospun blends of natural and synthetic polymer fibers as tissue engineering scaffolds'. Similarly, U.S. Pat. No. 7,704,740 'Nanofibrillar structure and applications including cell and tissue culture' describes the manufacturing of random oriented electrospun nanofibers with the aim to proliferate cell and tissue cultures. However, all these fibers used are made of polymers and produced in random ordering, despite the possibility of their particular arrangement later using different technologies.

SUMMARY OF THE INVENTION

An object of the present invention is to provide a novel biocompatible scaffold for multi-dimensional cultures of cells, providing a cell culture matrix that supports cells growth in a proper fashion, not requiring the optimization for individual cell types, but capable of inducing cell morphologies resembling the true cell (tissue) morphology, preserving the metabolism, receptors activation and protein expression in a way which resembles the true situation in the organism (in vivo).

It is an object of this invention to provide a biocompatible scaffold for multi-dimensional cultivation of cells, the scaffold comprising highly aligned fibers oriented to form a scaffold with open porosity for cultured cells, wherein the fibers have a diameter of 5-100 nm, and at the same time aspect ratio more than 10000:1, the fibers being made of non-cytotoxic, non-carcinogenic inorganic metal oxide, and the fibers being self-aligned into the scaffold during its manufacturing process.

It is an object of this invention to provide a scaffold for cultivation of stem cells for the purpose of automechanoinduction of neural differentiation of these stem cells, the scaffold comprising highly aligned fibers oriented to form a scaffold with open porosity over 70%, wherein the fibers have a diameter of less than 150 nm, preferably 20-50 nm and having aspect ratio more than 10000:1, preferably more than 20000:1, and wherein the fibers are made of non-cytotoxic, non-carcinogenic inorganic metal oxide, and the fibers are self-aligned into the scaffold during its manufacturing process.

It is another object of this invention to provide a method to induce automechanoinduction of neural differentiation of stem cells by cultivating the stem cells on a scaffold comprising highly aligned fibers oriented to form a scaffold with open porosity over 70%, wherein the fibers have a diameter of less than 150 nm, preferably 20-50 nm and having aspect ratio more than 10000:1, preferably more than 20000:1, and wherein the fibers are made of non-cytotoxic, non-carcinogenic inorganic metal oxide, and the fibers are self-aligned into the scaffold during its manufacturing process.

It is another object of this invention to provide a scaffold for cultivation of cancer cells for the purpose of automechanoinduction of gene expressions in these cancer cells to make them suitable as tumor models, the scaffold comprising highly aligned fibers oriented to form a scaffold with open porosity over 70%, wherein the fibers have a diameter of less than 150 nm, preferably 20-50 nm and having aspect ratio more than 10000:1, preferably more than 20000:1, and wherein the fibers are made of non-cytotoxic, non-carcinogenic inorganic metal oxide, and the fibers are self-aligned into the scaffold during its manufacturing process.

It is still another object of this invention to provide a method to induce automechanoinduction of gene expressions in cancer cells to make them suitable as tumor models, the method comprising cultivating the cancer cells on a scaffold comprising highly aligned fibers oriented to form a scaffold with open porosity over 70%, wherein the fibers have a diameter of less than 150 nm, preferably 20-50 nm and having aspect ratio more than 10000:1, preferably more than 20000:1, and wherein the fibers are made of non-cytotoxic, non-carcinogenic inorganic metal oxide, and the fibers are self-aligned into the scaffold during its manufacturing process.

According to a general embodiment of the invention a biocompatible scaffold for multi-dimensional cultivation of cells comprises self-aligned metal oxide fibers with ultra-high anisotropy, wherein the fibers have a diameter in the range of 5-100 nm with their aspect ratio more than 10000:1. In another embodiment the diameter of the fibers is about 20-50 nm and their aspect ratio simultaneously is more than 20000:1.

In any of the embodiments the scaffolds might contain additions, coatings, infiltrated factors and other features as desired by the user and as feasible for the specific cell culturing protocols. The scaffolds might be also used in any known or future cell culture system, testing and evaluation method to determine specific culture reactions.

The present invention provides a novel and inventive multi-dimensional cell culture system, which differs from known 2D and 3D systems (as shown in the practical examples), allowing cells to grow anisotropically (i.e. not equally, uniformly or randomly in all directions) in a specified milieu. The present invention gives principally new and non-conventional results concerning morphology, growth, proliferation, metabolism and differentiation of the different cell types.

The present invention opens up many possibilities to study mixtures of cells and influence of agents on the cells metabolism and behavior in vitro, reducing the number of animal in vivo models an early stage research.

The present invention provides a system where different cell types can be grown and therefore providing means to conduct comparable studies.

DETAILED DESCRIPTION OF THE INVENTION

Definitions

For the reasons of clarity, the terminology used in this description means:

"Fiber" refers to a fiber made of a non-cytotoxic, non-carcinogenic metal oxide, but not from polymers or bioactive ceramics (such as hydroxyapatite).

"Automechanoinduction" means an induction of a mechanical stimulus to a cell or tissue from their own interaction with the substrate or media, without application of an external force, comprising that this induction leads to changes in cells or tissues behavior, structure, functionality, morphology, or any other relevant property. Automechanoinduction also excludes application of specific culture media, where said changes in cells or tissues are caused by e.g. adjustment of biochemical or chemical composition.

"Bioinert" means a material which does not enter into biochemical reactions with live cells leading to changes in their shape, functionality, proliferation or fate, neither undergoes a destruction or transformations (bioresorbtion).

"Scaffold" refers to a structure comprising a self-aligned network of fibers made in situ.

"Randomly oriented fibers" refers to any fiber scaffold not fitting the description of the present invention, i.e. such fibers that have not been actively aligned or that do not follow any designed pattern of orientation to each other.

"Self-aligned fibers" refers to a structure that consists of one or more fibers that are highly oriented in parallel to each other during the structure manufacturing process, i.e. not during the separate packing of the fibers info the structure (assembly) after the fibers have been manufactured otherwise.

"Ultra-high anisotropy" refers to a self-aligned fibers scaffold which fibers have aspect ratios (length to diameter) of 10000:1 and more.

The present invention will now be described in more detail hereafter with reference to the accompanying examples and figures, in which embodiments of the invention are shown. This invention may, however, be embodied in many different forms and should not be construed as limited to the embodiments set forth herein.

Practical Examples

Methods Used

Figure 1:
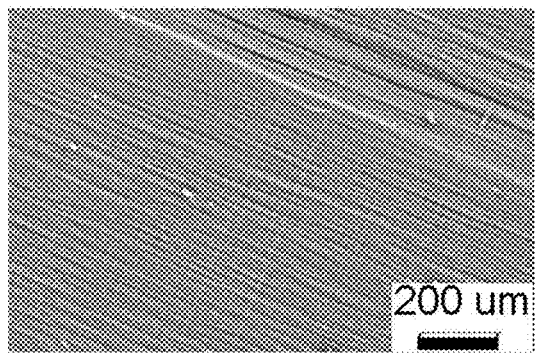
FIG. 1 shows the fine structure of the self-aligned fibrous scaffold made of metal oxide (alumina) nanofibers of ~40 nm diameter.

The scaffolds were manufactured from aluminum oxide based material (however, other oxides, such as silica, titania, zirconia could also be used) and heat treated with regimes determined by a thermal analysis study [9]. These self-aligned metal oxide fibers (FIG. 1) with an average single-fiber diameter of ~40 nm (TEM, HRSEM) and length of ~10-20 mm (aspect ratio ~$(10 \ldots 20) \cdot 10^3$ µm/$40 \cdot 10^{-3}$ µm=(250000 ... 500000):1) have 70-99% open porosity, preferably 85-95% open porosity (measured by BET and mercury porosimetry). Some of the scaffolds were also coated by graphene with catalyst-free chemical vapor deposition (CVD) at 1000° C. to demonstrate that coatings might be easily performed if required. On the contrary to other studies, graphene on the nanofibres was not functionalized in any way and became augmented to the underlying oxide fiber surface. Non-functionalized graphene was used as an example of bioinert material. Nanofibers with other average diameters like 7 and 25 nm and similar aspect ratios were also obtained, but most of the cell studies were conducted with 40 nm fiber scaffolds for consistency. No bioactive agents were added, nor other modification of the scaffolds was made, unlike most of their known studies, to exclude possible effects of bioactive additions on cells.

Human MSCs were obtained from freshly isolated subcutaneous adipose tissue and characterized as reported [10]. Cancer cell lines MDA-MB231, Caco2, WM239A and Kelly, were obtained from ATCC. Cells were grown in culture media (DMEM) with 10% FBS (fetal bovine serum), 1 mg/ml penicillin and 0.1 mg/ml streptomycin at 37° C. in 5% $CO_2$. The scaffolds were pre-treated for three days before the cells seeding by complete medium with changing the medium for fresh every 24 hours to saturate them by active components adsorbed from liquid phase (CellIn Technologies, Estonia).

For visualization of the cells, specific to filamentous actin (F-actin) phalloidin tagged by FITC (Sigma) was used. For hMSCs, pooled cells from three individuals with passage number below 5 were seeded on the scaffolds in 12-well plate ($4 \times 10^4$ cells per well). For cancer cells, $5 \times 10^4$ cells were added to the each well with scaffolds. Similar cells grown on a flat glass at the same density and cell culture conditions were considered as the controls. The cells were fixed by 4% PFA at 48 h after seeding, washed by PBS (phosphate buffered saline) and permeabilized by 0.3% TRITON X-100 in PBS for 5 minutes. Phalloidin-FITC (1:100) staining lasted for 18 h at 4° C. for scaffolds and 2 h at RT for controls. To stain the cells nucleus, cells were incubated for 10 minutes with Hoechst 33342 (Invitrogen, 1 µg/ml). After a final wash, the phalloidin-stained cells were analyzed by Nikon Eclipse 80i microscope (CellIn Technologies, Estonia).

Calculation of the orientations of hMSC seeded was used with "ImageJ" software and Orientation-J Distribution plug-in (version 1.50 g, National Institute of Health, USA). Original microscope images were converted into 8-bit color images and the pixels/distance ratio was calibrated based on the microscope camera bar. The images were threshold first by HSV color and then by brightness into binary images using Li algorithm. The orientation parameters were calculated with 5 pixel Gaussian window size and approximation with a cubic spline gradient. Finally, these data were treated with SigmaPlot software (Systat GmBH, Germany) into polar form.

Immunologic response for peripheral blood mononuclear cells (PBMCs) was evaluated using PBMCs from healthy donors, isolated using Ficoll-Paque gradient fractionation (CellIn Technologies, Estonia). $2 \times 10^6$ cells were used for each analysis. RNAs were extracted directly from scaffolds by TRIzol® (Ambion) reagent following 24 h cells growth on the scaffold, according to the manufacturer's recommendations. cDNAs were synthesized from DNase-treated (Ambion) RNA by RevertAid Reverse Transcriptase (Thermo Fisher Scientific) with addition of RiboLock (Thermo Fisher Scientific) according to the manufacturer's recommendations. cDNA quality was verified by RT-PCR by using GAPDH primers and HOT FIREpol® Master Mix (Solis Biodyne, Estonia). RT-qPCR was performed in triplicates using EvaGreen qPCR mix plus no Rox (Solis Biodyne, Estonia) and the LightCycler® 480 Real-Time PCR System (Roche Applied Science). The fold of change was calculated relatively to the control (cells grown without scaffolds) after normalization to GAPDH expression, using 2-ΔΔCt method (double difference of Ct). The values are respectively ΔCt=Ct(gene of interest)−Ct(GAPDH), and ΔΔCt=ΔCt(treated)−ΔCt(control). For visualization, the data were normalized to the cells grown without scaffold materials (control), converted to log scale and represented as a heat map (LionSolver 2.1, Reactive Search s.r.l., Italy). The minimal mapping error is achieved by minimizing sum of coordinates normalized with respect to the maximum and minimum along each dimension (in this case, decimal logarithm of relative expressions).

Secretome ELISA analysis was done from cell culture media collected with soluble factors expression was analysed 24 h after initiation of cell culture (Protobios, Estonia). The levels of IL6, IL8/CXCL8, CCL2, IL1B, IL2, IL4, IL12, TNFα and IFNγ secreted into the growth medium were measured using Human IL-6 DuoSet ELISA Development Kit (R&D System, Wiesbaden, Germany), Human IL-8 Standard ABTS ELISA Development Kit (Peprotech, Rock Hill, N.J., USA), Human CCL2/MCP-1 DuoSet (R&D System), Human IL-1β/IL-1F2 DuoSet ELISA Development Kit (R&D System, Wiesbaden, Germany), Human IL-2 ELISA Development Kit (Peprotech, Rock Hill, N.J., USA), Human IL-4 Standard ABTS (PeproTech, Rock Hill, N.J., USA), Human IL-12 ELISA Development Kit (Peprotech, Rock Hill, N.J., USA), Human TNFα ELISA Development Kit (Peprotech, Rock Hill, N.J., USA), Human IFN-γ ELISA Development Kit (Peprotech, Rock Hill, N.J., USA), and Human Standard ABTS ELISA Development Kit (Peprotech), respectively. The ELISA analysis was performed using high binding ELISA plates (Greiner BioOne) at RT according to the manufacturer's instructions. Optical density was measured using photospectrometer Spectramax 340 PC (Molecular Devices) at the wavelength 450 nm.

Figure 2:
FIG. 2 A, B shows contour morphology of the hMSC cultured on control (A) and new scaffolds (B), exhibiting preferential orientation.
Figure 2:

Example 1. Human Mesenchymal Stem Cells Cultured on New Scaffolds of this Invention Exhibit Preferential Orientation The morphology, adhesion and distribution of viable hMSC after 3 days of culture on horizontally oriented new scaffolds and on control (glass) are demonstrated in FIGS. 2A and B. The scaffolds under present invention were clearly guiding cells to line up along the fibers with a spindle-like shape and more than usually elongated lamellipodia extensions. High aspect ratio cellular orientations are developed throughout the scaffold, allowing directional connection between individual cells and formation of cells network. This confirms scaffolds do not impede the normal growth of stem cells. Furthermore, elongated morphology of hMSC and its high polarization create pre-requisites for preferential specific (e. g. neuronal or myogenic) lineage differentiation.

Whereas response of stem cells to different substrate stiffness was studied earlier, the inventors for the first time have found the effect of such ultra-high scaffold anisotropy in a self-aligned, highly porous state, which was not previously reported. Most of known nanofiber-based scaffolds are randomly oriented or loosely packed, making a 3D nanostructure without such stiffness anisotropy [for example, U.S. Pat. No. 7,704,740, US 20060263417, US 20070269481]. Many aligned fibrous scaffolds are made of polymer fibers, the intrinsic elastic modulus of which is less than oxide ceramics by few orders of magnitude. The effect observed at scaffolds under present invention differs also substantially from known nanotopology studies, where nano-grooves or other patterns are known to support cell alignment, but without local differences in substrate stiffness.

Figure 3A:
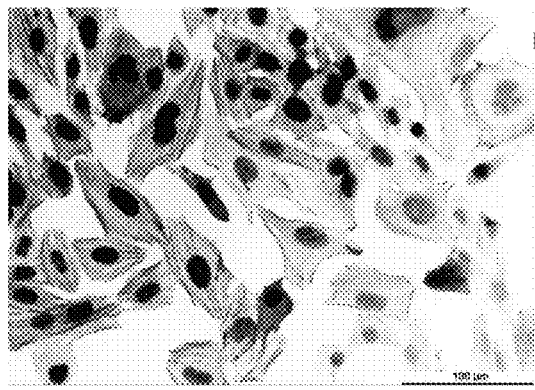
FIG. 3A, B shows images of the MDA-MB231 cancer cells cultures on the control (A) and new scaffolds (B).
Figure 3B:
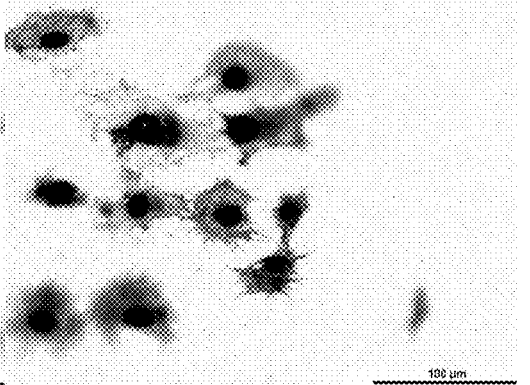

Example 2. MDA-MB231 Cancer Cells Grown on the New Scaffold of this Invention Show Extended Microspikes and Filopodia Protrusions Several cancer cell lines were seeded on the vertical and horizontal sides of the scaffolds of present invention. Cancer cells cultured on scaffolds possess extended microspikes and actin-rich filopodia protrusions suggesting high level of membrane activity and malignant migratory cancer phenotype (FIG. 3A,B shows MDA-MB231 cancer cell growth). The initial signs of cancer cell infiltration (and hence local immobilization of the cells) were detected on vertical fibers allowing suggestion of volumetric cancer model. By cancer cell infiltration, their reduced mobility and extended filopodia formation, scaffolds allow creating more representative phenotype necessary to obtain multi-dimensional in vitro cancer model that more accurately mimics tumor genesis. Furthermore, this model differs from both known 2D and 3D cultures as it allows partial immobilization of the cells into a "half-dimensional" direction (into the depth), keeping them unlimited to planar mobility. The inventors call this culture as 2.5D to emphasize this difference.

Figure 4:
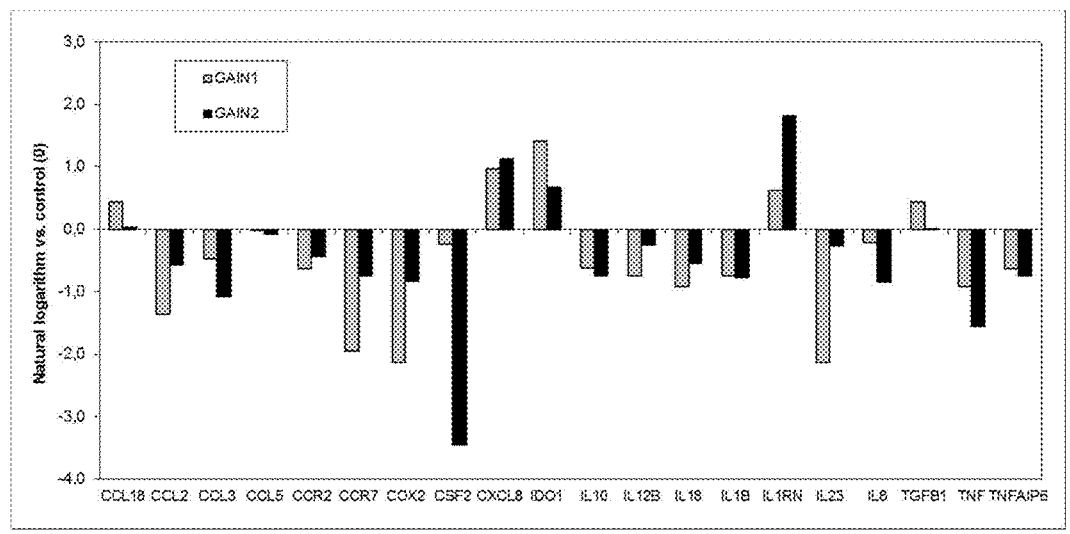
FIGS. 4 A and B shows gene expression heat maps for PBMC (A) and for hMSC (B) cultured on the scaffolds (all relative to control; note logaritmic scale which proves few orders of magnitude differences).
Figure 4B:
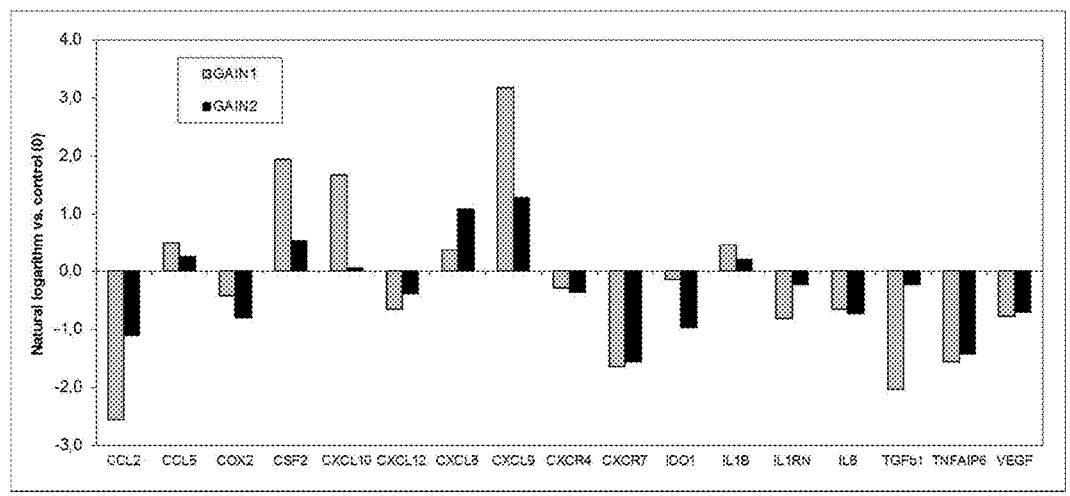

Example 3. Novel Scaffolds of this Invention have an Ability to Modulate Immune Response of Peripheral Blood Mononuclear Cells Immunological profiling of any material under the influence of in vivo or in vitro environment is an important content of biocompatibility evaluation and has a critical value for future clinical translation. In addition to hMSC (Example 1), this was assessed with PBMC as they are an important part of the human peripheral immune system, responsible for transforming of the multitude of external stimuli to generate an adaptive immune response. The PBMC were grown on the scaffolds and tissue culture plastic (control) in vitro, and their inflammatory signatures were compared (FIG. 4). The mRNA expression was analyzed for genes involved in the immune reaction and a secretion of cytokines (IL1B, TNFα, IFNγ, IL6, IL8, IL2, IL4, IL12B, and CCL2).

For PBMC, clear downregulation of pro-inflammatory TNF, IL1B, IL12B, IL6, CCL2 and COX2 cytokines was detected, demonstrating the strong ability of the scaffold to modulate immune response. Interestingly at the same time upregulated CCL18, IL1RN, IDO1 and TGFβ1 factors were observed. These factors participate in anti-inflammatory response, pointing out to the intrinsic possible immunomodulating effect of the scaffolds caused by their structure and composition alone, without any additions of external stimuli, which also was confirmed by ELISA (data not shown).

For hMSCs, the promoted mRNA expression of CXCL8, CXCL9, CXCL10 and CSF2, the chemokines participating in neutrophil, monocyte or leukocyte trafficking, were observed, indicating the possible changes in chemotaxis. Additionally, reduced expression of COX2, CCL2 and IL6 cytokines indicates a good immune tolerance of these scaffolds.

The present invention provides a principally new solution overcoming the drawbacks known by prior art by providing a 2.5-dimensional biocompatible scaffold designed for various cell cultures, capable to provide novel and more efficient methods for cell and drug research as well as tissue engineering applications.

Other features and uses of the invention and their associated advantages will be evident to a one skilled in the art upon reading the description and the examples.

REFERENCES

1. Lee, J., Cuddihy, M. J., Kotov, N. A. Three-dimensional cell culture matrices: state of the art. *Tissue Eng Part B Rev* 14, 61-86 (2008)
2. Bressan, E. et al. Graphene based scaffolds effects on stem cells commitment. *J Translational Medicine* 12, 296 (2014)
3. Jin, G., Li, K. The electrically conductive scaffold as the skeleton of stem cell niche in regenerative medicine. *Materials Sci and Eng. C* 45, 671-681 (2014)
4. Smith, L. A. et al. Directed differentiation and neurite extension of mouse embryonic stem cell on aligned poly(lactide) nanofibers functionalized with YIGSR peptide, *Biomaterials* 34 (2013) 9089-9095.
5. Talukdar, Y. et al. The effects of graphene nanostructures on mesenchymal stem cells. *Biomaterials* 35 (2014) 4863-4877
6. Discher, D. E., Janmey, P., Wang, Y.-L. Tissue cells feel and respond to the stiffness of their substrate. *Science* 310, 1139-43 (2005)
7. Coulombe, P. A., Wong, P. Cytoplasmic intermediate filaments revealed as dynamic and multipurpose scaffolds. *Nat Cell Biol* 6, 699-706 (2004)
8. Kenny, P. A. et al. The morphologies of breast cancer cell lines in three-dimensional assays correlate with their profiles of gene expression. *Mol Oncol* 1, 84-96 (2007)
9. Aghayan, M., Hussainova, I., Gasik, M., Kutuzov, M., Friman, M. Coupled thermal analysis of novel alumina nanofibers with ultrahigh aspect ratio. *Thermochim Acta* 574, 140-144 (2013)
10. Kazantseva, J. et al. Alternative splicing targeting the hTAF4-TAFH domain of TAF4 represses proliferation and accelerates chondrogenic differentiation of human mesenchymal stem cells. *PLoS One* 8(10):e74799 (2013)

What is claimed is:

1. A biocompatible scaffold for multi-dimensional cultivation of cells, said scaffolds capable of automechanoinduction and comprising:
    aligned fibers oriented to form a scaffold with open porosity for the cultured cells, wherein the fibers have a diameter of 5-100 nm, and an aspect ratio more than 10000:1,
    said fibers being made of non-cytotoxic, non-carcinogenic inorganic metal oxide, and
    said fibers being self-aligned into the scaffold during its manufacturing process.
2. The scaffold according to claim 1, wherein the open porosity is in a range of 70-99%.
3. The scaffold according to claim 2, wherein the open porosity is 85-95%.
4. The scaffold according to claim 1, wherein the fibers have a length of 10-20 mm.
5. The scaffold according to claim 1, wherein the diameter of the fibers is 20-50 nm.
6. The scaffold according to claim 1, wherein the fibers have aspect ratio more than 20000:1.
7. The scaffold according to claim 1, wherein the fibers are coated with a bioinert material.
8. The scaffold according to claim 7, wherein the bioinert material is non-functionalized graphene.
9. The scaffold according to claim 1, wherein the metal oxide is selected from the group consisting of silica, titania, zirconia and alumina.
10. The scaffold of according to claim 9, wherein the fibers are of aluminum oxide.
11. The scaffold of claim 1, wherein the scaffold is for cultivation of stem cells and the scaffold is capable of inducing automechanoinduction of neural differentiation of the stem cells.
12. The scaffold of claim 1, wherein the scaffold is for cultivation of cancer cells and the scaffold is capable of inducing automechanoinduction of gene expressions in the cancer cells to make them suitable as tumor models.

13. A method to induce automechanoinduction of neural differentiation of stem cells by cultivating the stem cells on a scaffold of claim 1.

14. A method to induce automechanoinduction of gene expressions in cancer cells by cultivating the cancer cells on a scaffold of claim 1.

\* \* \* \* \*